US008840551B2

(12) United States Patent
Matott (10) Patent No.: US 8,840,551 B2
(45) Date of Patent: Sep. 23, 2014

(54) TETHERING CAPSULE SYSTEM

(75) Inventor: Laura A Matott, East Aurora, NY (US)

(73) Assignee: Given Imaging, Inc., Duluth, GA (US)

( * ) Notice: Subject to any disclaimer, the term of this patent is extended or adjusted under 35 U.S.C. 154(b) by 871 days.

(21) Appl. No.: 12/973,443

(22) Filed: Dec. 20, 2010

(65) Prior Publication Data

US 2011/0152639 A1 Jun. 23, 2011

Related U.S. Application Data

(60) Provisional application No. 61/288,419, filed on Dec. 21, 2009.

(51) Int. Cl.
| | | |
|---|---|---|
| A61B 5/07 | (2006.01) | |
| A61B 5/145 | (2006.01) | |
| A61B 5/06 | (2006.01) | |
| A61B 1/00 | (2006.01) | |
| A61B 5/01 | (2006.01) | |
| A61B 1/04 | (2006.01) | |
| A61B 5/03 | (2006.01) | |

(52) U.S. Cl.
CPC ............ *A61B 5/073* (2013.01); *A61B 5/14539* (2013.01); *A61B 1/00036* (2013.01); *A61B 5/01* (2013.01); *A61B 5/062* (2013.01); *A61B 1/041* (2013.01); *A61B 5/036* (2013.01)
USPC .......................................... 600/302

(58) Field of Classification Search
CPC ......... A61B 1/041; A61B 5/036; A61B 5/073
USPC ....................................... 600/302
See application file for complete search history.

(56) References Cited

U.S. PATENT DOCUMENTS

| 3,042,030 A | 7/1962 | Read |
|---|---|---|
| 4,278,077 A | 7/1981 | Mizumoto |

(Continued)

FOREIGN PATENT DOCUMENTS

| DE | 344 0177 | 5/1986 |
|---|---|---|
| JP | 57-45833 | 3/1982 |

(Continued)

OTHER PUBLICATIONS

Office Action for Japanese Application No. 2006-351272 mailed Feb. 28, 2012.

(Continued)

*Primary Examiner* — Michael D'Angelo
*Assistant Examiner* — Christian Jang
(74) *Attorney, Agent, or Firm* — Pearl Cohen Zedek Latzer Baratz LLP (57) ABSTRACT

A capsule system comprising a first capsule (16) configured to be ingested by a subject, a second capsule (18) configured to be ingested by the subject separately from the first capsule, the first capsule having an electromagnetic element (29, 30) and a sensor (22, 23) for sensing a physiological parameter of a gastrointestinal tract of the subject, the second capsule having a magnetic element (29, 30) and a sensor (22, 23) for sensing a physiological parameter of the gastrointestinal tract of the subject, the first capsule and the second capsule having an active state wherein a magnetic force is selectively provided between the first and second capsules attracting the first and second capsules while the capsules are within the gastrointestinal tract of the subject and having an inactive state wherein the magnetic force is absent, and a control (26/32) configured to selectively place the capsules in the active state from the inactive state while the capsules are within the gastrointestinal tract of the subject.

29 Claims, 10 Drawing Sheets

(56) References Cited

U.S. PATENT DOCUMENTS

| | | | |
|---|---|---|---|
| 4,626,213 | A | 12/1986 | Shiner et al. |
| 5,604,531 | A | 2/1997 | Iddan et al. |
| 5,662,587 | A | 9/1997 | Grundfest et al. |
| 5,681,260 | A | 10/1997 | Ueda |
| 5,993,212 | A | 11/1999 | Shiner |
| 5,993,378 | A | 11/1999 | Lemelson |
| 6,240,312 | B1 | 5/2001 | Alfano et al. |
| 6,350,076 | B1 | 2/2002 | Wagner et al. |
| 6,627,206 | B2 | 9/2003 | Lloyd |
| 6,936,003 | B2 | 8/2005 | Iddan |
| 6,951,536 | B2 | 10/2005 | Yokoi et al. |
| 7,182,089 | B2 | 2/2007 | Ries |
| 7,192,397 | B2 | 3/2007 | Lewkowicz et al. |
| 7,442,166 | B2 | 10/2008 | Huang et al. |
| 7,678,043 | B2 | 3/2010 | Gilad |
| 2001/0035902 | A1 | 11/2001 | Iddan et al. |
| 2002/0103417 | A1 | 8/2002 | Gazdzinski |
| 2002/0173718 | A1 | 11/2002 | Frisch |
| 2003/0018280 | A1 | 1/2003 | Lewkowicz et al. |
| 2004/0122315 | A1 | 6/2004 | Krill |
| 2004/0143182 | A1 | 7/2004 | Kucera et al. |
| 2004/0199054 | A1 | 10/2004 | Wakefield |
| 2004/0264754 | A1 | 12/2004 | Kleen |
| 2006/0036166 | A1 | 2/2006 | Horn |
| 2006/0149386 | A1 | 7/2006 | Clarke et al. |
| 2006/0231110 | A1 | 10/2006 | Mintchev |
| 2007/0032699 | A1 | 2/2007 | Segawa et al. |
| 2007/0043263 | A1 | 2/2007 | Wakefield |
| 2007/0099469 | A1 | 5/2007 | Sorensen |
| 2007/0161862 | A1 | 7/2007 | Yokoi et al. |
| 2007/0173691 | A1 | 7/2007 | Yokoi et al. |
| 2007/0173696 | A1 | 7/2007 | Fujimori et al. |
| 2008/0114204 | A1* | 5/2008 | Fujimori et al. ............ 600/130 |
| 2010/0130837 | A1* | 5/2010 | Matott ........................ 600/302 |

FOREIGN PATENT DOCUMENTS

| | | |
|---|---|---|
| JP | 4-008342 | 1/1992 |
| JP | 4-109927 | 4/1992 |
| JP | 1992-144533 | 5/1992 |
| JP | 6-114037 | 4/1994 |
| JP | 2002-000556 A | 1/2002 |
| JP | 2004-321796 | 11/2004 |
| JP | 2007-181682 | 7/2007 |
| SU | 1768945 | 10/1992 |
| WO | WO 2004-058041 | 7/2004 |
| WO | WO 2005-112460 | 11/2005 |

OTHER PUBLICATIONS

Swallowable devices join-up for a mission, www.medicaldesign.com, dated Oct. 6, 2008.

Building a Self-Assembling Stomach-Bot, www.technologyreview.com, dated Oct. 22, 2008.

Robotic Repair kit for the body, www.cordis.europa.eu, (2006).

* cited by examiner

TETHERING CAPSULE SYSTEM

CROSS-REFERENCE TO RELATED APPLICATIONS

This application claims the benefit of U.S. Provisional Patent Application No. 61/288,419, filed Dec. 21, 2009. The entire content of such application is incorporated by reference herein.

TECHNICAL FIELD

The present invention relates generally to ingestible capsules and, more particularly, to a magnetic ingestible capsule system.

BACKGROUND ART

Ingestible capsules are well-known in the prior art. Such capsules are generally small pill-like devices that can be ingested or swallowed by a patient. It is known that such capsules may include one or more sensors for determining physiological parameters of the gastrointestinal tract, such as sensors for detecting temperature, pH and pressure.

U.S. Patent Publication No. US2004/0122315 discloses multiple individual ingestible medical payload carrying capsules having the ability to wirelessly communicate among themselves.

U.S. Pat. No. 6,627,206 discloses a method and apparatus for treating obesity with individual space-filling portions having a magnetic insert that are used to form a space-filling polyhedron or other space-filling shape in the stomach of a patient.

The Swiss Federal Institute of Technology has tested the use of permanent magnets to connect different modules in the stomach. Testing was conducted to determine how well modules linked together by monitoring changes to the field of each magnet.

It is also known that certain physiological parameters may be associated with regions of the gastrointestinal tract. For example, a 1988 article entitled "Measurement of Gastrointestinal pH Profiles in Normal Ambulant Human Subjects" discloses pH measurements recorded by a capsule passing through the gastrointestinal tract. It is known that pH has been correlated with transitions from the stomach to the small bowel (gastric emptying) and from the distal small bowel to the colon (ileo-caecal junction).

BRIEF SUMMARY OF THE INVENTION

With parenthetical reference to corresponding parts, portions or surfaces of the disclosed embodiment, merely for the purposes of illustration and not by way of limitation, the present invention provides a capsule system comprising a first capsule (16) configured to be ingested by a subject, a second capsule (18) configured to be ingested by the subject separately from the first capsule, the first capsule having an electromagnetic element (29, 30) and a sensor (22, 23) for sensing a physiological parameter of a gastrointestinal tract of the subject, the second capsule having a magnetic element (29, 30) and a sensor (22, 23) for sensing a physiological parameter of the gastrointestinal tract of the subject, the first capsule and the second capsule having an active state wherein a magnetic force is selectively provided between the first and second capsules attracting the first and second capsules while the capsules are within the gastrointestinal tract of the subject and having an inactive state wherein the magnetic force is absent, and a control (26/32) configured to selectively place the capsules in the active state from the inactive state while the capsules are within the gastrointestinal tract of the subject.

The magnetic element may be an electromagnet, or may be selected from a group consisting of an electromagnet, a permanent magnet and ferrous material. The control may comprise a microprocessor (26) and a switch (32) connected to the electromagnet. The control may comprise an actuator configured to move the magnetic element from a first position to a second position closer to an outside surface of the capsule than the first position. The first capsule may comprise a receiver configured to receive a signal from exterior of the gastrointestinal tract of the subject and wherein the control places the capsules in the active state as a function of the signal. The sensor may provide a signal as a function of the physiological parameter of the gastrointestinal tract of the subject and the control may place the capsules in the active state as a function of the signal, and the control may place the capsules in the active state when the sensor senses the parameter above or below a selected amount. The control may be configured to selectively place the capsules in the inactive state from the active state while the capsules are within the gastrointestinal tract of the subject. The first capsule may comprise a receiver configured to receive a signal from exterior of the gastrointestinal tract of the subject and the control may place the capsules in the inactive state as a function of the signal. The sensor may provide a signal as a function of the physiological parameter of the gastrointestinal tract of the subject and the control may place the capsules in the inactive state as a function of the signal, and the control may place the capsules in the inactive state when the sensor senses the parameter above or below a selected amount.

The control may be configured to selectively place the capsules in the inactive state from the active state while the capsules are within the gastrointestinal tract of the subject, the first capsule may comprise a receiver configured to receive a signal from exterior of the gastrointestinal tract of the subject, and the control may place the capsules in the active state or the inactive state as a function of the signal. The control may be configured to selectively place the capsules in the inactive state from the active state while the capsules are within the gastrointestinal tract of the subject, the sensor may provide a signal as a function of the physiological parameter of the gastrointestinal tract of the subject, and the control may place the capsules in the active state or the inactive state as a function of the signal. The control may be configured to automatically place the capsules in the inactive state after a selected time lapse from the control placing the capsules in the active state. The capsule may further comprise a transmitter (28) communicating with the sensor and may further comprise a receiver (20) adapted to receive data transmitted from the transmitter.

The magnetic elements of the first and second capsules may be electromagnets that both provide a first polarity causing a repelling magnetic force between said capsules when said capsules are in said inactive state. The control may place the capsules in the active state by changing the first polarity of the electromagnet of the first capsule to a second polarity causing an attracting magnetic force between the capsules when the capsules are in the active state.

In another aspect the invention comprises a first capsule configured to be ingested by a subject, a second capsule configured to be ingested by the subject separately from the first capsule, the first capsule having an electromagnetic element and a sensor for sensing a physiological parameter of a gastrointestinal tract of the subject, the second capsule having an electromagnetic element and a sensor for sensing a physiological parameter of the gastrointestinal tract of the subject, the first capsule and the second capsule having an active state wherein a magnetic force is provided by the first and second capsules while the capsules are within the gastrointestinal tract of the subject and having an inactive state wherein the magnetic force is absent, and a control configured to selectively activate the active state of each of the capsules while the capsules are within the gastrointestinal tract of the subject.

The control may be configured to activate the capsules in an order in which they exit from a stomach of the gastrointestinal tract of the subject. Each of the capsules may further comprise a unique identifier and a transmitter communicating with the sensor, and may further comprise a receiver adapted to receive data transmitted from the transmitter. The receiver may be configured to receive data from each capsule and to correlate the data with the unique capsule identifier. The sensor may comprise a pressure sensor (22) for sensing pressure within the gastrointestinal tract of the subject. The capsule may further comprise a processor programmed to detect a migrating motor complex of the gastrointestinal tract of the subject as a function of the pressure.

In another aspect, the invention comprises a first capsule (16) configured to be ingested by a subject, a second capsule (18) configured to be ingested by the subject separately from the first capsule, a third capsule (19) configured to be ingested by the subject separately from the first and second capsule, the first capsule having an electromagnetic element and a sensor for sensing a physiological parameter of a gastrointestinal tract of the subject, the second capsule having an electromagnetic element and a sensor for sensing a physiological parameter of the gastrointestinal tract of the subject, the third capsule having an electromagnetic element and a sensor for sensing a physiological parameter of the gastrointestinal tract of the subject, the first capsule, the second capsule and the third capsule having an active state wherein a magnetic force is provided by the first, second and third capsules while the capsules are within the gastrointestinal tract of the subject and having an inactive state wherein the magnetic force is absent, and a control configured to selectively activate the active state of each of the capsules while the capsules are within the gastrointestinal tract of the subject.

The control may be configured to activate the first capsule prior to activation of the second capsule and to activate the second capsule prior to activation of the third capsule. The control may be configured to activate the capsules in the order in which they exit from a stomach of the gastrointestinal tract of the subject. The capsules may further comprise a transmitter communicating with the sensor and may further comprise a receiver adapted to receive data transmitted from the transmitter external to the gastrointestinal tract of the subject. The sensor may comprise a pressure sensor for sensing pressure within the gastrointestinal tract of the subject.

Accordingly, an object is to provide a capsule system in which multiple capsules may be connected and disconnected while in the gastrointestinal tract of a subject.

Another object is to provide a capsule system capable of detecting a migrating motor complex in the gastrointestinal tract of the subject.

These and other objects and advantages will become apparent from the foregoing and ongoing written specification, the drawings, and the claims.

DESCRIPTION OF THE PREFERRED EMBODIMENTS

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Figure 1:
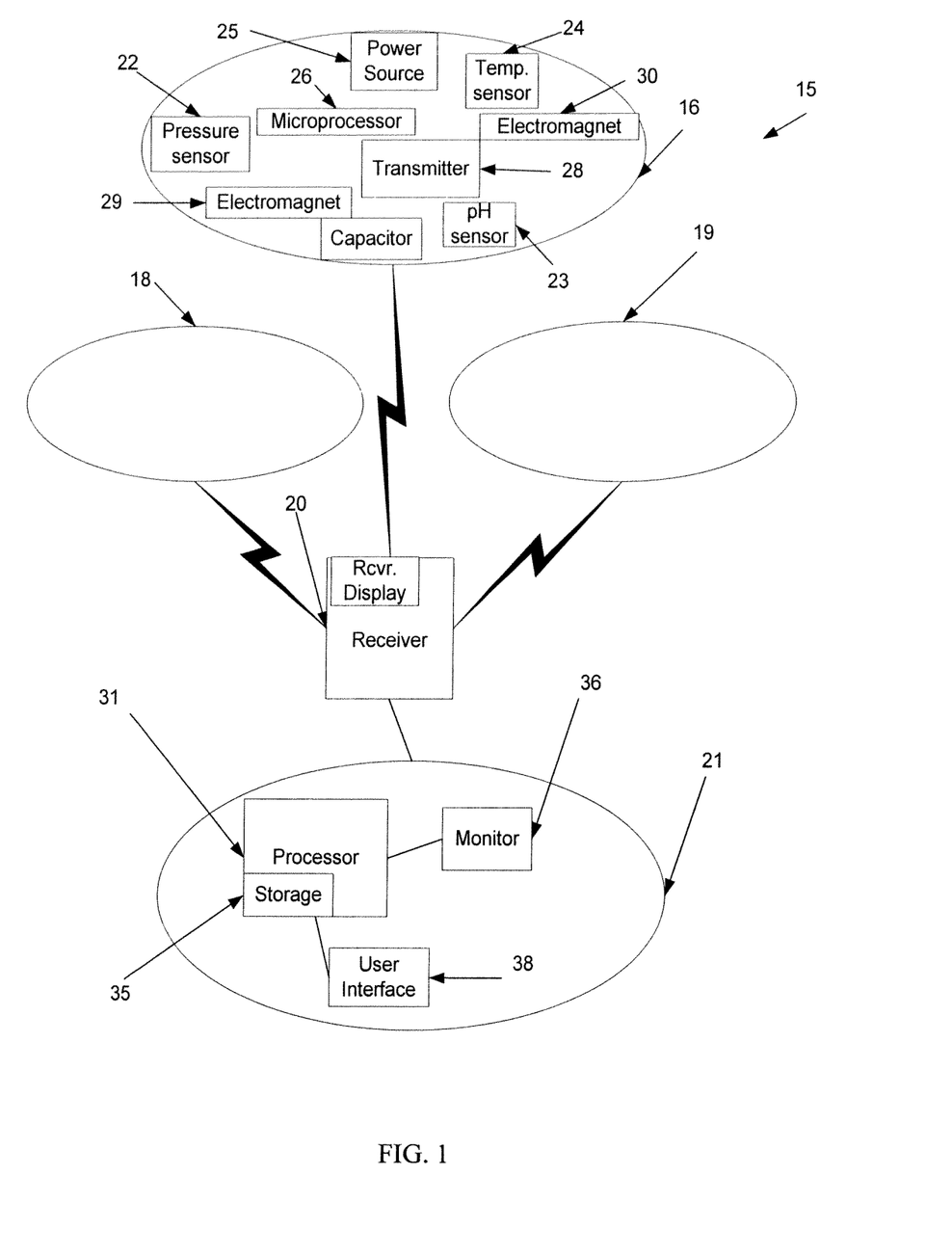
FIG. 1 is a schematic view of an embodiment of the improved capsule system.

Referring now to the drawings, and more particularly to FIG. 1 thereof, this invention provides a capsule system for evaluating the gastrointestinal tract of a subject, of which a first embodiment is generally indicated at 15. As shown in FIG. 1, system 15 generally includes multiple electromagnetic capsules 16, 18 and 19, receiver 20, and computer workstation 21.

In this embodiment, receiver 20 is configured to receive and store signals sent from transmitter 28. However, capsules 16, 18 and 19 may also include a receiving chip and receiver 20 may be configured to send signals to the capsules.

Computer workstation 21 includes processor 31 and is programmed to process measurements from pressure sensor 22, pH sensor 23 and temperature sensor 24.

Figure 2:
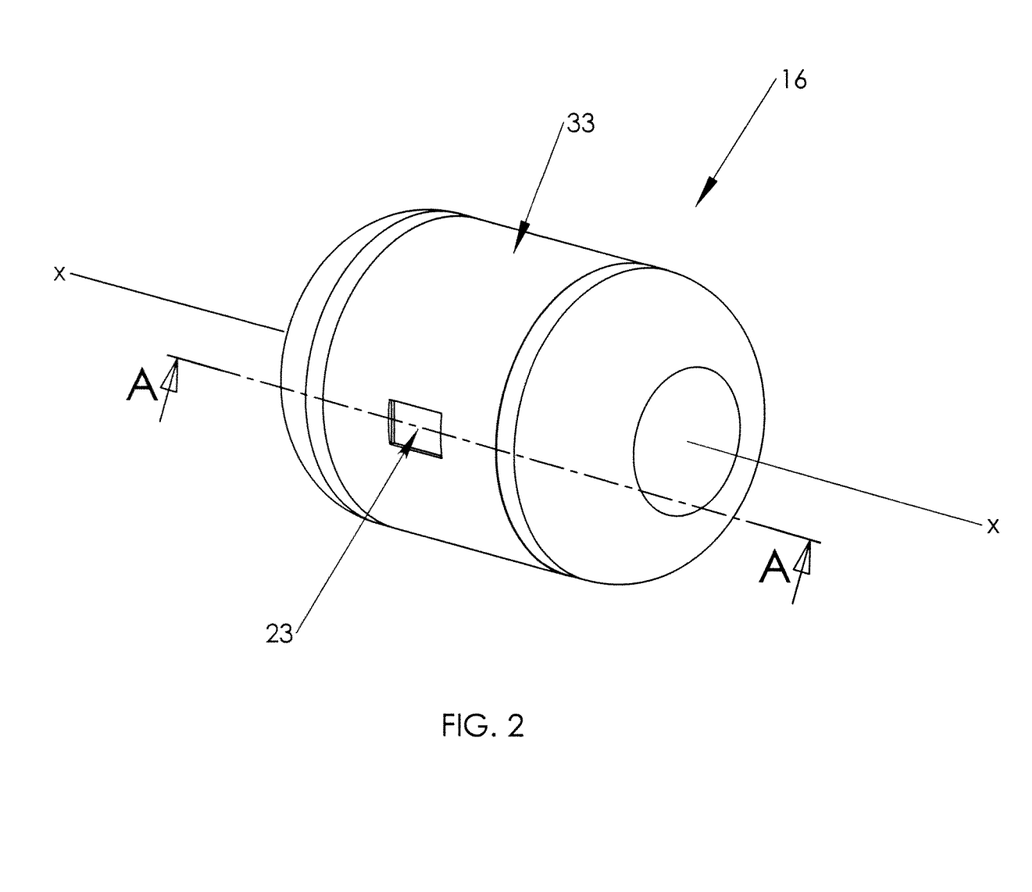
FIG. 2 is a perspective view of an embodiment of the capsule shown in FIG. 1.

As shown in FIG. 2, capsules 16, 18 and 19 are ellipsoid-shaped devices elongated about axis x-x, somewhat resembling a medicament capsule. The capsules generally have a hard shell or casing 33 which houses the transmitting electronics, a battery compartment, power supply 25, microprocessor 26, electromagnets 29 and 30, and sensors 22, 23 and 24. Capsules 16, 18 and 19 are adapted to be ingested or otherwise positioned within a tract to sense pressure, pH and temperature within the tract and to transmit such readings. The capsules are generally provided with an outer surface to facilitate easy swallowing and are autonomous self-contained swallowable capsules. Thus, capsules 16, 18 and 19 do not require any wires or cables to, for example, receive power or transmit information. The pH, pressure and temperature data are transmitted from within the GI tract to data receiver 20 outside the subject's body.

Figure 3:
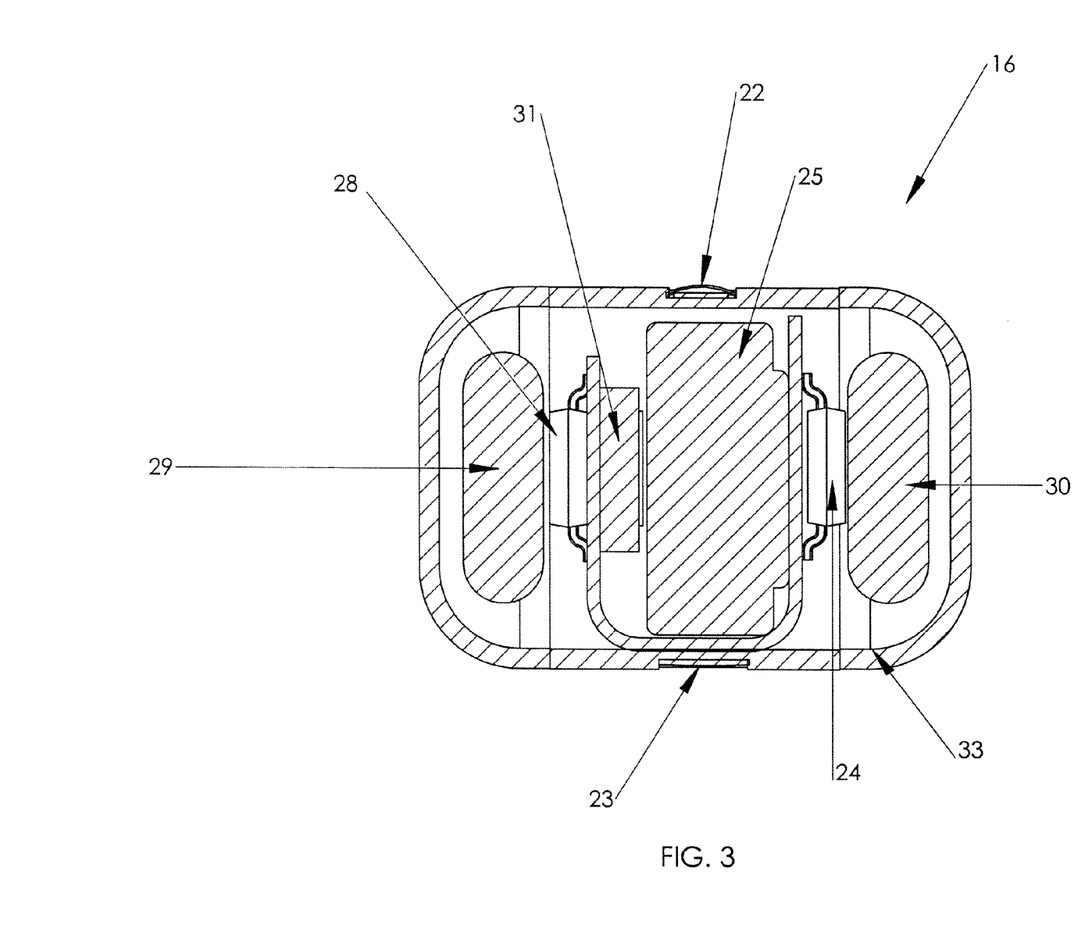
FIG. 3 is a longitudinal horizontal sectional view of a capsule shown in FIG. 2, taken generally on line A-A of FIG. 2.

As shown in FIG. 3, each of capsules 16, 18 and 19 include pressure sensor assembly 22, pH sensor 23 and temperature sensor 24 for taking measurements of pressure, pH and temperature, respectively, of a subject's gastrointestinal tract. Capsules 16, 18 and 19 also included power source 25, microprocessor 26, transmitter 28 and electromagnets 29 and 30. Each of capsules 16, 18 and 19 is identified by a unique serial number.

In this embodiment, power supply 25 is a lithium battery, although it is contemplated that other batteries may be used, such as a silver-oxide battery. Power supply 25 is adapted to power the electrical components of the capsule when in the gastrointestinal tract of a subject. To maximize its operation life, battery 25 is activated just prior to ingestion by way of an activation switch adapted to turn the capsule on and off. In this embodiment, the activation switch is a circuit operating between battery 25 and the electrical components that selectively powers on and off the electronic components by way of a magnetic sensor which responds selectively to the presence, absence and/or polarity of a magnetic field. A number of conventional switches may be used. For example, an "active" reed switch system may be used, in which an external magnetic field actively holds a reed switch so that the circuit remains open. When the ingestible capsule is removed from the magnetic field, the reed switch closes the circuit, thereby activating the capsule. An alternative method is to use a passive reed switch and a magnetizable bias magnet asymmetric design manipulated by an external magnet. The circuitry of the capsule is selectively switched on and off depending on the magnetic state of the bias magnet, which determines the reed switch on/off state. The magnetic activation and deactivation circuit disclosed in U.S. patent application Ser. No. 11/899,316 entitled "Magnetic Activation and Deactivation Circuit and System," the entire disclosure of which is incorporated herein by reference, may also be used in this embodiment.

In this embodiment, transmitter 28 is a radio frequency (RF) transmitter that transmits measurements from the capsule when it is in the gastrointestinal tract of a subject to remote receiver 20. Transmitter 28 transmits measurements at about 434 MHz. Portable data receiver 20 worn by the subject receives and stores the measurements transmitted by transmitter 28 for later download through a docking station to Windows PC compatible computer 21, such as a conventional laptop or a desktop. An antenna amplifies the transmit power of transmitter 28 so that it can be received by remote receiver 20.

In this embodiment, the capsules each include a temperature sensor 24. Temperature sensors 24 may be used to compensate or provide a baseline relative to the other sensors in the subject capsule.

In this embodiment, pressure sensor assembly 22 is a piezoelectric pressure sensor die on the surface of shell 33 that measures dynamic pressures by deforming when compressed, causing the generation of electric charges which are proportional to the pressure applied. Alternatively, the pressure sensor assembly may comprise a chamber between an inner wall and a flexible membrane of shell 33 filled with a fluid. A rigid PCB arm extends into the chamber and supports a conventional piezoelectric bridge. As fluid presses against the bridge, it creates an electrical signal which corresponds to the pressure of fluid in the chamber. The fluid is a non-compressible medium that forms part of the 360° degree force sensing mechanism for the sensor. Thus, pressure sensor 22 is operatively arranged to sense pressure within the gastrointestinal tract.

In this embodiment, pH sensor 23 comprises a conventional ISFET type pH sensor on one side with a pH reference electrode on the other. ISFET stands for ion-selective field effect transistor and the sensor is derived from MOSFET technology (metal oxide screen field effect transistor). A current between a source and a drain is controlled by a gate voltage. The gate is composed of a special chemical layer which is sensitive to free hydrogen ions (pH). Versions of this layer have been developed using aluminum oxide, silicon nitride and titanium oxide. Free hydrogen ions influence the voltage between the gate and the source. The effect on the drain current is based solely on electrostatic effects, so the hydrogen ions do not need to migrate through the pH sensitive layer. This allows equilibrium, and thus pH measurement, to be achieved in a matter of seconds. The sensor is an entirely solid state sensor, unlike glass bulb sensors which require a bulb filled with buffer solution. Only the gate surface is exposed to the sample. As the output from pH sensor 23 is an analog signal, an analog to digital converter is provided to convert the signal from sensor 23 to a digital signal.

In this embodiment, the range and accuracy of sensors 23, 22 and 24 are generally 1 to 9.0 pH units with an accuracy of ±0.5 pH units, 0 to 350 mmHg with an accuracy of 5 mmHg, or 10% above 100 mmHg, and 25° to 49° C. with an accuracy of ±1° C., respectively.

Micro-processor 26 is connected to and communicates with pressure sensor 22 and pH sensor 23. Processor 26 controls the sampling rate of sensors 22 and 23 and is also connected to transmitter 28 to control the RF transmission frequency and the information and data being transmitted. Processor 26 also processes signals received from pH sensor 23 and temperature sensor 24 and provides command or control signals to electromagnets 29 and 30 as a function of such sensor readings, as further described below.

Figure 4:
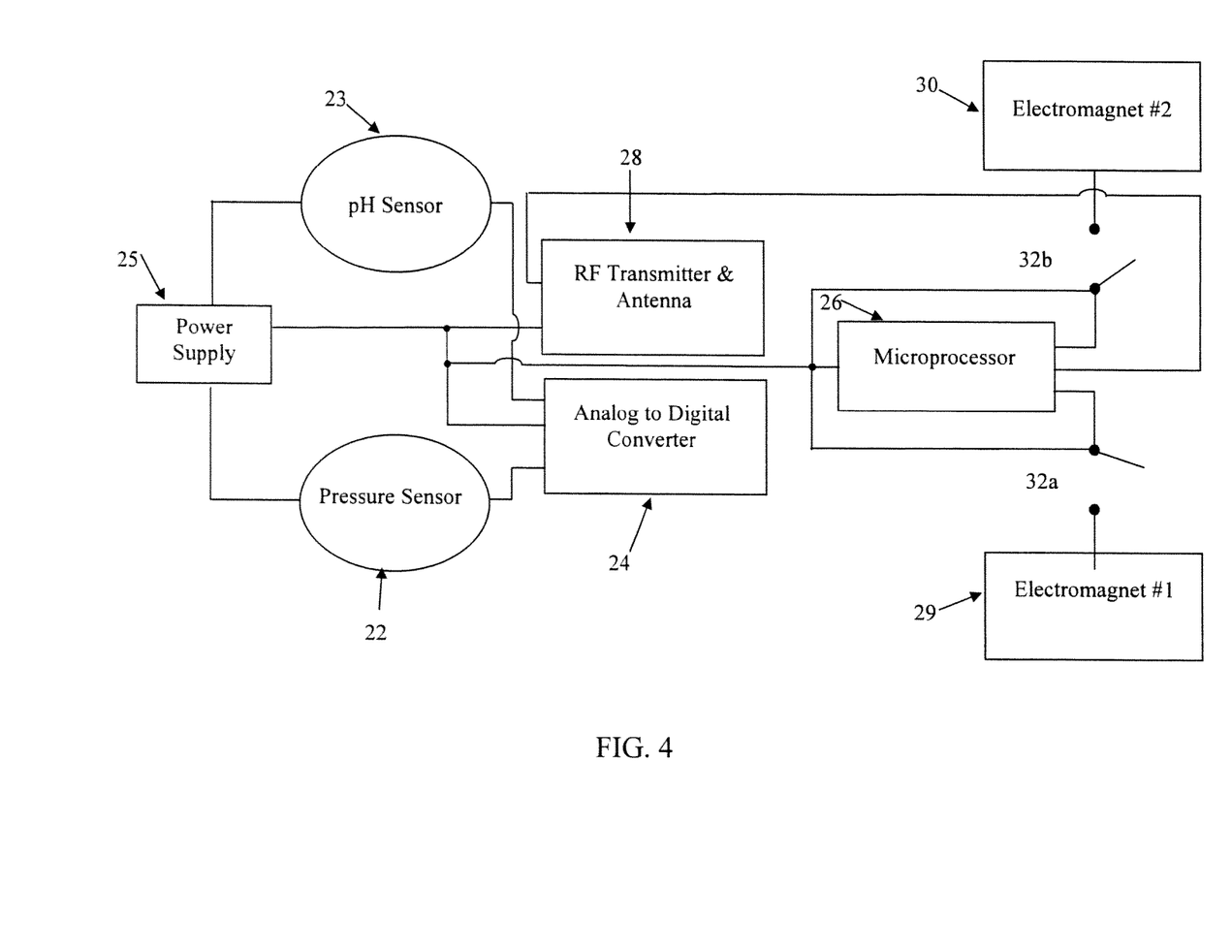
FIG. 4 is a schematic of the capsule shown in FIG. 3.

As shown in FIGS. 3 and 4, capsules 16, 18 and 19 include electromagnets 29 and 30 orientated at each end of the capsule. In this embodiment, electromagnets 29 and 30 are conventional micro-electromagnets in which the magnetic field is produced by an electric current flowing through a conductor. When the electric current ceases the magnetic field is no longer produced. The magnetic field created is defined by the geometrical and structural shape of the conductor. The orientation of the magnetic field is dependent on the direction of current flow.

Figure 5:
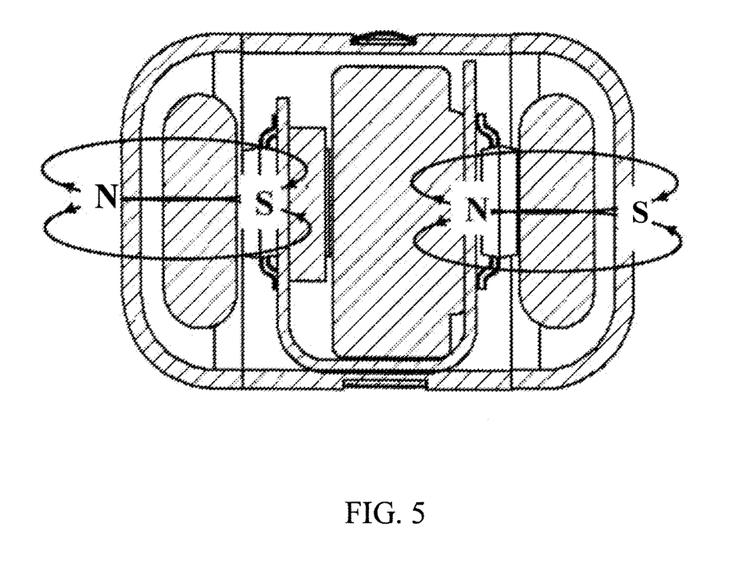
FIG. 5 is a view of the capsule shown in FIG. 3 in an active state with resulting electromagnetic fields.
Figure 6:
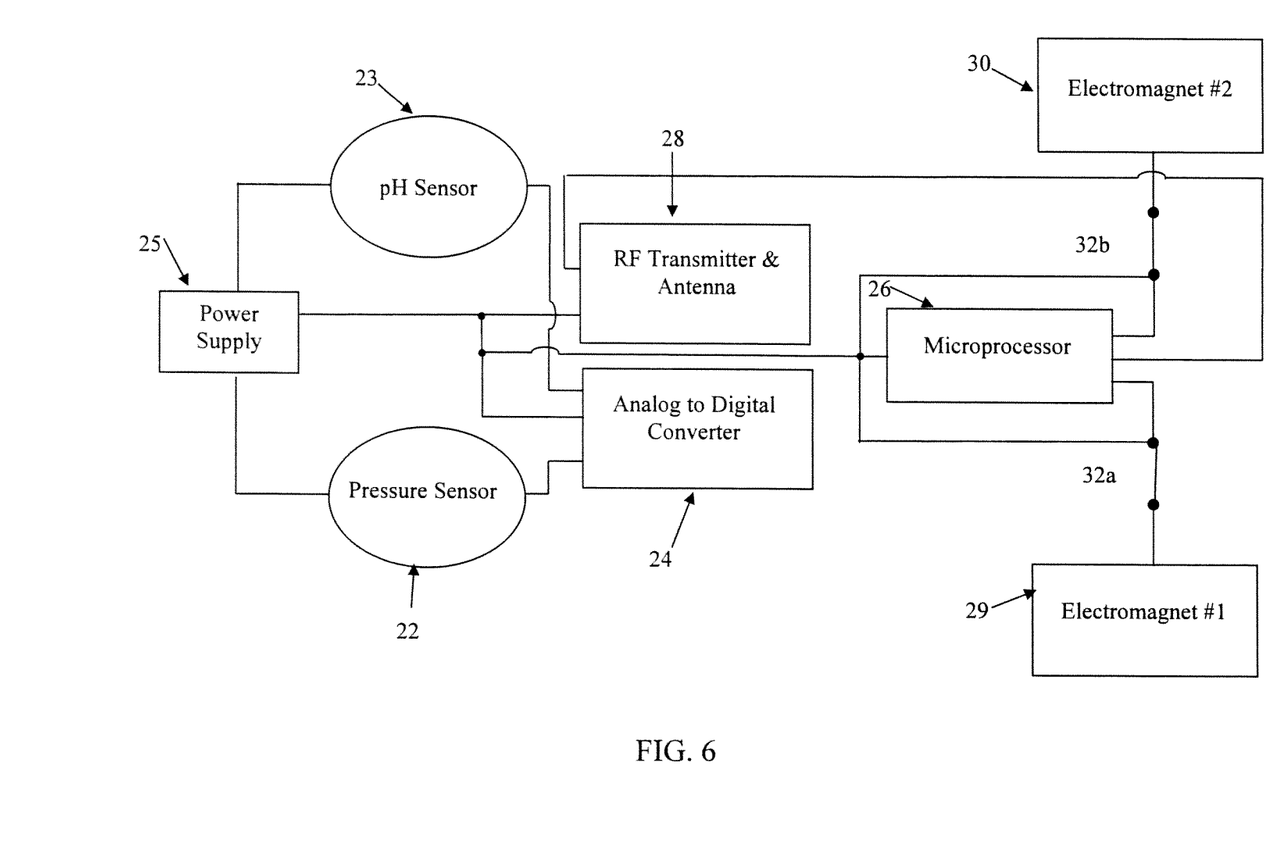
FIG. 6 is a schematic of the capsule shown in FIG. 5.

As shown in FIGS. 4 and 6, electromagnetic activation switches 32a and 32b are controlled by microprocessor 26. When switches 32a and 32b are open, as shown in FIG. 4, electromagnets 29 and 30 are not powered and the capsule is in a non-magnetic or inactive state. However, when switches 32a and 32b are closed, as shown in FIG. 6, electromagnets 29 and 30, respectively, are powered with an electric current. When powered, electromagnets 29 and 30 create an electromagnetic field, as shown in FIG. 5. This electromagnetic field causes the capsules to attract at opposite poles and thereby link up in the gastrointestinal tract.

The user of system 15 selects the number of capsules the user desires the subject to ingest, powers the capsules using the capsule activation system, and has the subject ingest the capsules one at a time in a fasting state. The user also enters into receiver 20 and/or computer 21 the number of capsules ingested by the subject. While three capsules are used in this embodiment of the system, the number of capsules may be varied, as described further below.

Switches 32a and 32b are maintained in an open position when ingested by the subject so that the capsules are not magnetic when ingested. Microprocessor 26 is configured to closes switches 32a and 32b based upon pH readings from pH sensor 23. When the capsules are powered, pH sensor 23 on each capsule takes measurements and such measurements are transmitted to microprocessor 26.

A pH reading below 4.0 indicates normal acidic conditions in the stomach of a subject. Microprocessor 26 records the pH data from sensor 23 against a comparator to determine gastric emptying. Gastric emptying is identified by the start of a sustained pH rise. The pH profile of gastric emptying is typically characterized by a sharp rise in pH from very low values, followed by slight drop, and concluded by a sustained pH at around neutral value. This corresponds with the exit of the capsule from the highly acidic environment of the stomach into the small bowel, were is at a neutral level for healthy subjects. Microprocessor 26 detects gastric emptying by identifying a sharp increase in the pH data. The beginning point of the rise is the point of gastric emptying. Microprocessor 26 uses this point to activate the electromagnetic field of the subject capsule by closing switches 32a and 32b and thereby powering electromagnets 29 and 30, respectively, which create the electromagnetic field shown in FIG. 5.

Figure 7:
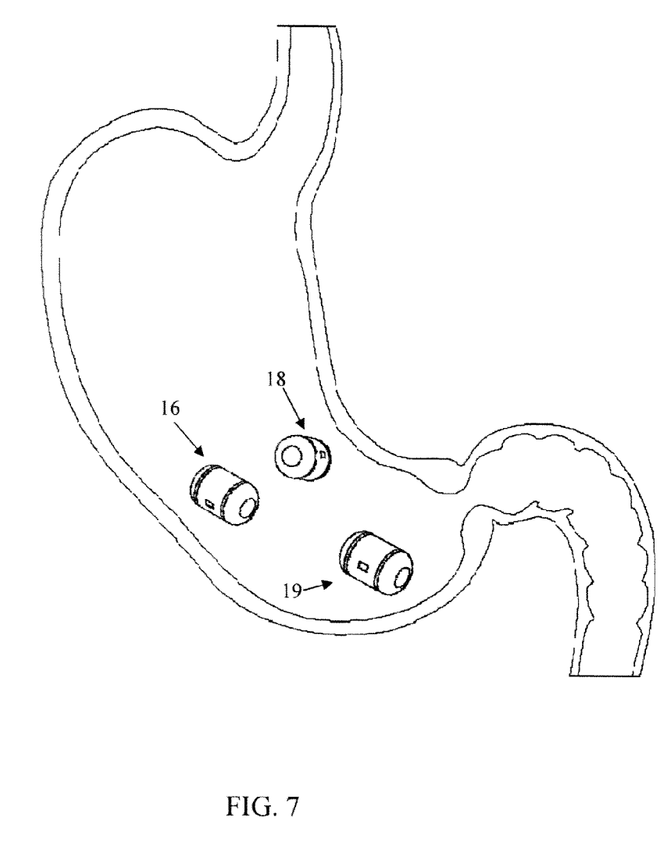
FIG. 7 is a view of multiple capsules in the stomach of a subject shortly after ingestion with the capsules in an inactive state.
Figure 8:
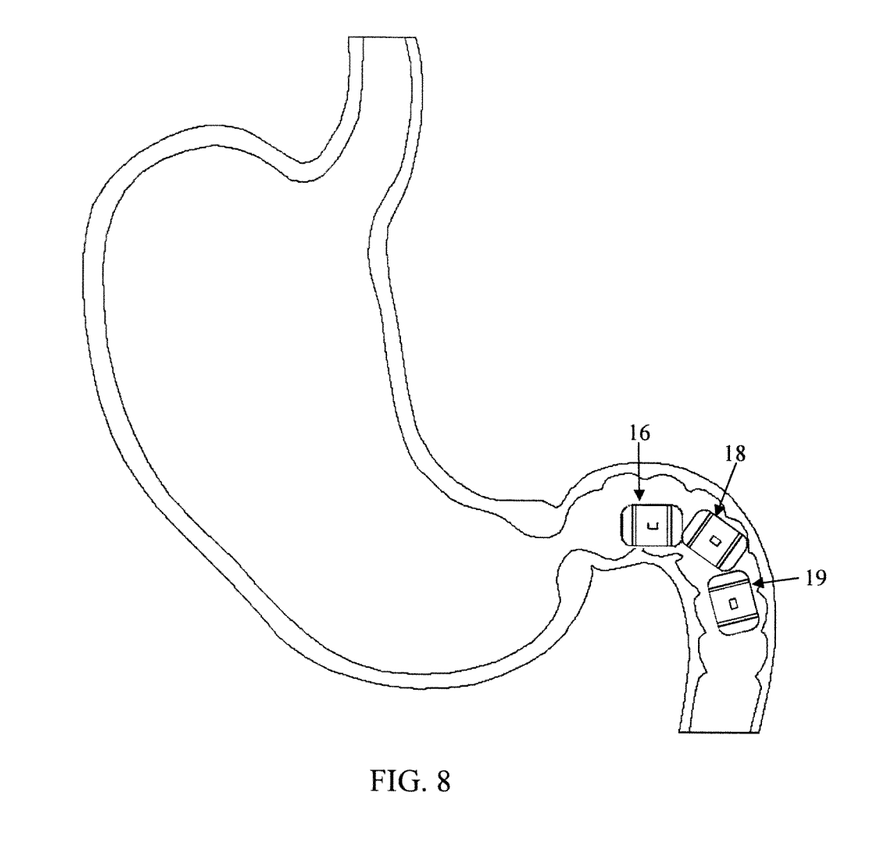
FIG. 8 is a view of the capsules shown in FIG. 7 after exiting the stomach and with the capsules in an active state.

Electromagnet 29 generates a north pole at the front end of the subject capsule and electromagnet 30 generates a south pole at the rear end of the subject capsule. When two such activated capsules are in close proximity, the north pole of the first capsule will be attracted to and will join with the south pole of the second capsule. The capsules thereby attract each other and form a chain as they progress through the intestinal tract of the subject, as shown in FIG. 8. Thus, as shown in FIG. 7, in an inactive state, capsules 16, 18 and 19 are not tethered. However, based on measurements taken by pH sensor 23 and an increase in such measurements indicating that the subject capsule has moved from the stomach into the small intestines of the subject, the capsules are activated and form a chain as they empty the stomach, as shown in FIG. 8.

In addition to activation of electromagnets 29 and 30, microprocessor 26 also uses measurements taken by pH sensor 23 and an increase in such measurements indicating that the subject capsule has moved from the stomach into the small intestines of the subject to activate and begin transmitting measurements taken by pressure sensor 22 from transmitter 28. Readings are taken from pressure sensor 22 in each of capsules 16, 18 and 19, as well as pH sensor 23 and temperature sensor 24, as the chain of capsules passes through the intestinal tract of a subject and are transmitted once the capsules exit the stomach. The raw data measurements are transmitted in data packets to receiver 20, which is outside the gastrointestinal tract of the subject. Data packets are marked with each capsule's unique serial number. Once microprocessor 26 senses a pH increase and activates the capsule, the activation time and serial number are recorded to determine the order of the capsules as they exit the stomach.

Figure 9:
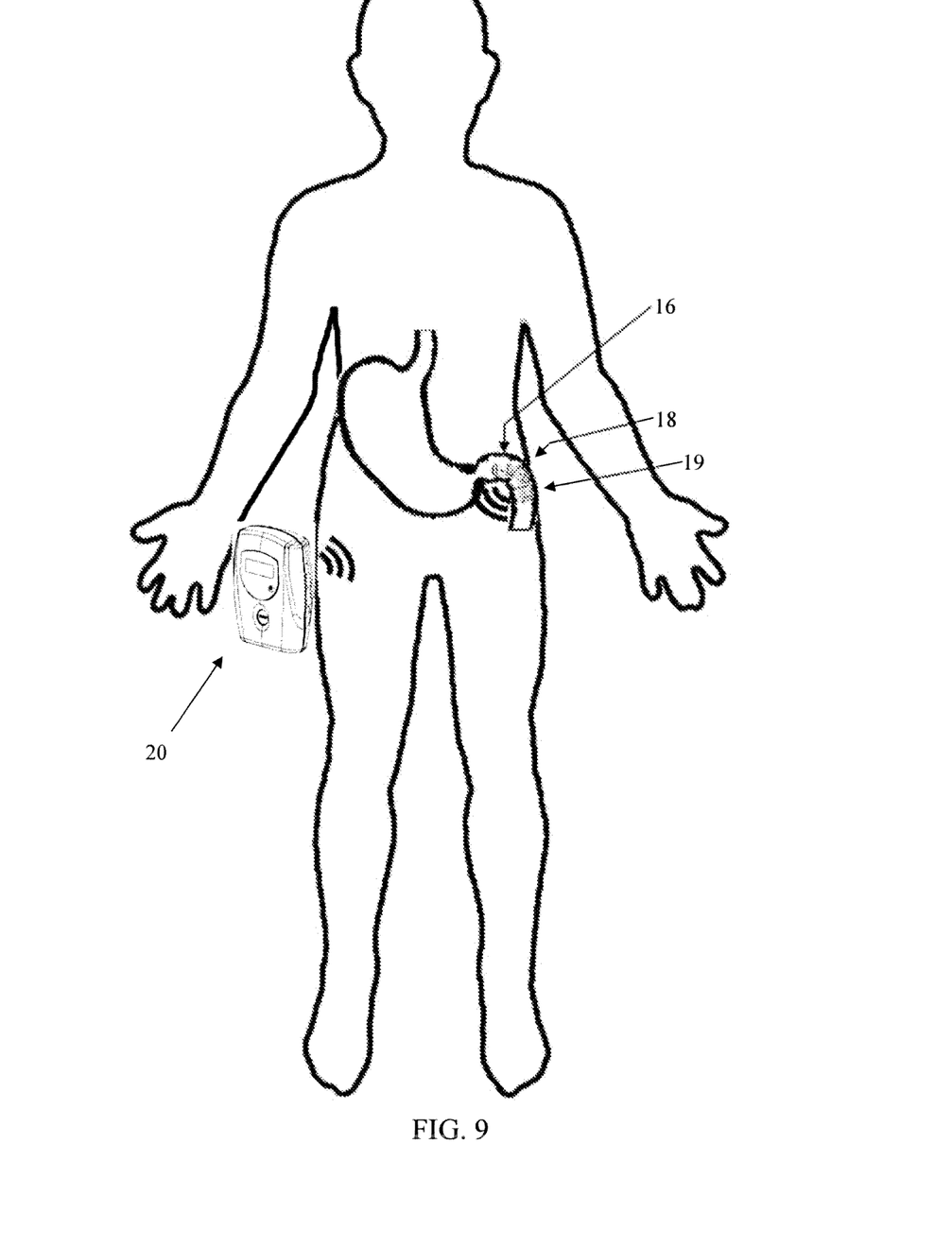
FIG. 9 is a representative view of the capsules shown in FIG. 8 in communication with a receiver worn by a subject.

As shown in FIG. 9, portable data receiver 20 is worn by the subject and receives and stores the data packets transmitted by transmitters 28 in capsules 16, 18 and 19. Data receiver 20 contains rechargeable batteries and when seated in a docking station allows for battery charging and data download. Data is downloaded from data receiver 20 through a docking station via a USB connection to a Windows PC compatible computer 21, such as a conventional laptop or a desktop. After the recording period is complete, receiver 20 is seated in a docking station connected to computer 21, which transfers the data from receiver 20 to computer 21.

In this embodiment, personal computer 21 includes a processor 31, data processing storage 35, a monitor or display 36 and a user input device 38. In this embodiment, monitor 36 is a computer screen. However, monitor 36 may be any other device capable of providing an image or other data. In this embodiment, user input device 38 includes a keyboard and a mouse. However, it could be any other suitable input-output device to data processor 31.

The processing and analysis of the pressure, temperature, and pH measurements from each of capsules 16, 18, and 19 is generally provided using computer-executable instructions executed by a general-purpose computer, such as a server or personal computer 21. However, it should be noted that this processing and analysis may be practiced with other computer system configurations, including internet appliances, hand-held devices, wearable computers, multi-processor systems, programmable consumer electronics, network PCs, mainframe computers and the like. The term computer or processor as used herein refers to any of the above devices as well as any other data processor. Some examples of processors are microprocessors, microcontrollers, CPUs, PICs, PLCs, PCs or microcomputers. A computer-readable medium comprises a medium configured to store or transport computer readable code, or in which computer readable code may be embedded. Some examples of computer-readable media are CD-ROM disks, ROM cards, floppy disks, flash ROMS, RAM, nonvolatile ROM, magnetic tapes, computer hard drives, conventional hard disks, and servers on a network. The computer systems described above are for purposes of example only. An embodiment of the invention may be implemented in any type of computer system or programming or processing environment. In addition, it is meant to encompass processing that is performed in a distributed computing environment, were tasks or modules are performed by more than one processing device or by remote processing devices that are run through a communications network, such as a local area network, a wide area network or the internet. Thus, the term processor is to be interpreted expansively.

Figure 10:
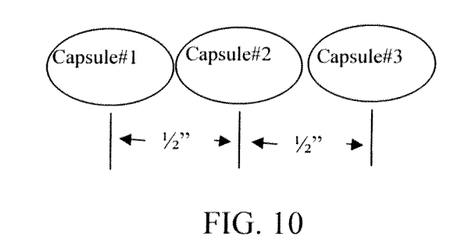
FIG. 10 is a representative view of the capsule linking configuration shown in FIG. 8.

Processor 31 is programmed to extract information from the pressure measurements taken by the string of pressure sensors 22 in the gastrointestinal tract of the subject to identify migratory motor complexes (MMCs). MMCs are a cyclic pattern of contractions through the stomach and small intestine of a subject during fasting. As shown in FIG. 10, with a chain of three capsules in the small bowel, three pressure sensors spaced ½ inches apart are taking measurements. Readings from all three sensors spaced ½ inch apart may be used to identify MMCs, or readings from just two sensors spaced 1 inch part may be used to identify MMCs. In particular, pressure readings for each capsule are separately plotted against time and compared. MMCs are characterized by isolated bursts of pressure spikes that progress along the digestive tract. These isolated bursts of pressure spikes can be identified in readings taken by at least two pressure sensors spaced apart in the digestive tract.

Figure 11:
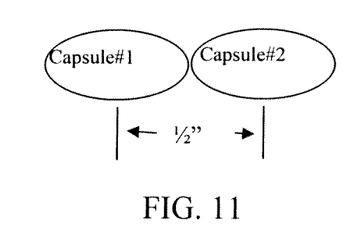
FIG. 11 is a representative view of a second capsule linking configuration.

FIG. 11 shows an embodiment in which a string or chain of two tethered capsules is used rather than three. As shown, in this embodiment sensor readings from just two pressure sensors spaced ½ inch part are used to identify MMCs. In this embodiment it is not necessary for both capsules to have an electromagnet. One capsule has an electromagnet and the second capsule may have a permanent magnet or ferrous material.

In this embodiment, the capsules may also be active upon ingestion with a polarity at the end of each capsule that is the same, causing the capsules to repel. Based on an externally-activated signal or a sensed parameter, the polarity is then changed so that the capsules are of opposite polarity and attract each other. The polarity may be later returned to the same polarity for both capsules so that they repel and detach, again based on an externally-activated signal or a sensed parameter.

Figure 12:
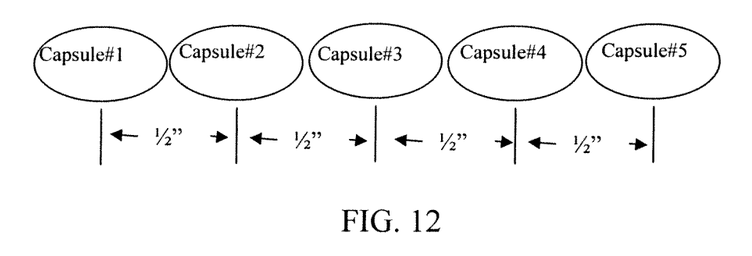
FIG. 12 is a representative view of a third capsule linking configuration.

FIG. 12 shows an embodiment in which a string or chain of five tethered capsules is used rather than three. As shown, readings from sensors at multiple different spacings may be used to identify MMCs. For example, sensor readings from two sensors spaced 2 inches apart may be used (capsule 1 and capsule 5), sensor readings from three sensors spaced 1 inch apart may be used (capsule 1, capsule 3 and capsule 5), or sensor readings from 5 sensors spaced ½ inch apart (all capsules) may be used. Other combinations in terms of the number of sensors and the spacing between the sensors may be used as desired.

Microprocessor 26 may be programmed to automatically open switches 32a and 32b to deactivate the electromagnetic field after a period of time has lapsed. After such pre-programmed length of time, microprocessor 26 automatically deactivates the capsules so that they become untethered. This mechanism allows for any tethered capsules to separate and pass through the digestive tract individually.

In another embodiment, microprocessor 26 may deactivate the electromagnets based on sensor readings indicating that the capsule has passed through the ileo-cecal junction (ICJ). The ICJ is indicated by a minimum pH drop of 0.7 units, and typically occurs 0.5-6 hours after gastric emptying of the capsule in healthy patients.

Receiver 20 may also contain an emergency deactivation button, which when pressed by the subject will signal microprocessor 26 to deactivate the tethered capsules by opening switches 32a and 32b and cancelling the magnetic field. The subject is directed to press the emergency button when the subject feels any discomfort.

In another embodiment, electromagnets 29 and 30 may be activated by a signal transmitted from a point external to the subject's body based on data received by receiver 20, such as pH data indicating that the capsule has emptied from the subject's stomach. In this embodiment, capsules 16, 18 and 19 include a receiver to receive signals from a transmitter external to the subject's body, which sends the signal to close switches 32a and 32b and activate the electromagnets. Alternatively, the user may transmit a signal to activate the electromagnets based on sensor readings received by and displayed on the display screen of receiver 20.

In another embodiment, microprocessor 26 may be programmed to activate capsules 16, 18 and 19 in a specific order. For example, microprocessor 26 may be programmed to activate capsules 16, 18 and 19 at specific points in time after ingestion. Alternatively, microprocessor 26 may be programmed to activate capsules 16, 18 and 19 in a predetermined order using the unique capsule serial numbers.

It is also contemplated that spacer capsules that do not include pressure sensors may be utilized in the system. In this embodiment, the spacer capsules are used to increase the distance between the capsules that do contain pressure sensors. Microprocessor 26 is programmed to activate a first capsule having a pressure sensor, followed by the desired number of spacer capsules, followed by a second capsule having a pressure sensor. Other configurations could be employed. For example, the second capsule having a pressure sensor could be followed by one or more additional spacer capsules, followed in turn by a third capsule having a pressure sensor.

While these embodiments have been described in relation to the gastrointestinal tract of a human, it is contemplated that the system may be used in connection with the gastrointestinal tract of other animals.

The present invention contemplates that many changes and modifications may be made. Therefore, while the presently-preferred form of the system has been shown and described, and a number of alternatives discussed, persons skilled in this art will readily appreciate that various additional changes and modifications may be made without departing from the spirit of the invention, as defined and differentiated by the following claims.

What is claimed is:

1. A capsule system comprising:
    a first capsule configured to be ingested by a subject;
    a second capsule configured to be ingested by said subject separately from said first capsule;
    said first capsule having an electromagnetic element and a sensor for sensing a physiological parameter of a gastrointestinal tract of said subject;
    said second capsule having a magnetic element and a sensor for sensing a physiological parameter of said gastrointestinal tract of said subject;
    each said first capsule and said second capsule having an active state wherein a magnetic force is selectively provided between said first and second capsules attracting said first and second capsules while said capsules are within said gastrointestinal tract of said subject and having an inactive state wherein said attracting magnetic force is absent; and
    a control configured to selectively place each of said capsules in said active state from said inactive state while said capsules are within said gastrointestinal tract of said subject.

2. The system set forth in claim 1, wherein said magnetic element is an electromagnet.

3. The system set forth in claim 1, wherein said control comprises a microprocessor and a switch connected to said electromagnet.

4. The system set forth in claim 1, wherein said control comprises an actuator configured to move said magnetic element from a first position to a second position closer to an outside surface of said capsule than said first position.

5. The system set forth in claim 1, wherein said first capsule comprises a receiver configured to receive a signal from exterior of said gastrointestinal tract of said subject and wherein said control places said capsule in said active state as a function of said signal.

6. The system set forth in claim 1, wherein said sensor of said first and/or second capsule provides a signal as a function of said physiological parameter of said gastrointestinal tract of said subject and said control places said capsules in said active state as a function of said signal.

7. The system set forth in claim 6, wherein said control places said capsules in said active state when said sensor senses said parameter above or below a selected amount.

8. The system set forth in claim 1, wherein said control is configured to selectively place said capsules in said inactive state from said active state while said capsules are within said gastrointestinal tract of said subject.

9. The system set forth in claim 8, wherein said first capsule comprises a receiver configured to receive a signal from exterior of said gastrointestinal tract of said subject and wherein said control places said capsules in said inactive state as a function of said signal.

10. The system set forth in claim 8, wherein said sensor of said first and/or second capsule provides a signal as a function of said physiological parameter of said gastrointestinal tract of said subject and said control places said capsules in said inactive state as a function of said signal.

11. The system set forth in claim 10, wherein said control places said capsules in said inactive state when said sensor senses said parameter above or below a selected amount.

12. The system set forth in claim 1, wherein: said control is configured to selectively place said capsules in said inactive state from said active state while said capsules are within said gastrointestinal tract of said subject; said first capsule comprises a receiver configured to receive a signal from exterior of said gastrointestinal tract of said subject; and said control places said capsules in said active state or said inactive state as a function of said signal.

13. The system set forth in claim 1, wherein: said control is configured to selectively place said capsules in said inactive state from said active state while said capsules are within said gastrointestinal tract of said subject; said sensor of said first and/or second capsule provides a signal as a function of said physiological parameter of said gastrointestinal tract of said subject; and said control places said capsules in said active state or said inactive state as a function of said signal.

14. The system set forth in claim 13, wherein said control places said capsules in said active state when said sensor senses said parameter above said selected amount and places said capsule in said inactive state when said sensor senses said parameter below said selected amount.

15. The capsule system set forth in claim 1, wherein said control is configured to automatically place said capsules in said inactive state after a selected time lapse from said control placing said capsules in said active state.

16. The capsule system set forth in claim 1, wherein said capsule further comprises a transmitter communicating with said sensor of said first and/or second capsule and further comprising a receiver adapted to receive data transmitted from said transmitter.

17. The capsule system set forth in claim 1, wherein said magnetic elements of said first and second capsules are electromagnets that both provide a first polarity causing a repelling magnetic force between said capsules when said capsules are in said inactive state.

18. The capsule system set forth in claim 17, wherein said control is configured to selectively place said capsules in said active state by changing said first polarity of said electromagnet of said first capsule to a second polarity causing an attracting magnetic force between said capsules when said capsules are in said active state.

19. A capsule system comprising:
a first capsule configured to be ingested by a subject;
a second capsule configured to be ingested by said subject separately from said first capsule;
said first capsule having an electromagnetic element and a sensor for sensing a physiological parameter of a gastrointestinal tract of said subject;
said second capsule having an electromagnetic element and a sensor for sensing a physiological parameter of said gastrointestinal tract of said subject;
each of said first capsule and said second capsule having an active state wherein a magnetic force is provided by said first and second capsules while said capsules are within said gastrointestinal tract of said subject and having an inactive state wherein said magnetic force is absent; and
a control configured to selectively activate said active state of each of said capsules while said capsules are within said gastrointestinal tract of said subject.

20. The capsule system set forth in claim 19, wherein said control is configured to activate said capsules in an order in which they exit from a stomach of said gastrointestinal tract of said subject.

21. The capsule system set forth in claim 19, wherein each of said capsules further comprises a unique identifier and a transmitter communicating with said sensor of said first and/or second capsule, and further comprising a receiver adapted to receive data transmitted from said transmitter.

22. The capsule system set forth in claim 21, wherein said receiver is configured to receive data from each capsule and to correlate said data with said unique capsule identifier.

23. The capsule system set forth in claim 22, wherein said sensor of said first and/or second capsule comprises a pressure sensor for sensing pressure within said gastrointestinal tract of said subject.

24. The capsule system set forth in claim 23, and further comprising a processor programmed to detect a migrating motor complex of said gastrointestinal tract of said subject as a function of said pressure.

25. A capsule system comprising:
a first capsule configured to be ingested by a subject;
a second capsule configured to be ingested by said subject separately from said first capsule;
a third capsule configured to be ingested by said subject separately from said first and second capsule;
said first capsule having an electromagnetic element and a sensor for sensing a physiological parameter of a gastrointestinal tract of said subject;
said second capsule having an electromagnetic element and a sensor for sensing a physiological parameter of said gastrointestinal tract of said subject;
said third capsule having an electromagnetic element and a sensor for sensing a physiological parameter of said gastrointestinal tract of said subject;
said first capsule, said second capsule and said third capsule having an active state wherein a magnetic force is provided by said first, second and third capsules while said capsules are within said gastrointestinal tract of said subject and having an inactive state wherein said magnetic force is absent; and
a control configured to selectively activate said active state of each of said capsules while said capsules are within said gastrointestinal tract of said subject.

26. The capsule system set forth in claim 25, wherein said control is configured to activate said first capsule prior to activation of said second capsule and to activate said second capsule prior to activation of said third capsule.

27. The capsule system set forth in claim 26, wherein said control is configured to activate said capsules in the order in which they exit from a stomach of said gastrointestinal tract of said subject.

28. The capsule system set forth in claim 25, wherein said capsule further comprises a transmitter communicating with said sensor of said first and/or second capsule, and further comprises a receiver adapted to receive data transmitted from said transmitter external to said gastrointestinal tract of said subject.

29. The capsule system set forth in claim 28, wherein said sensor comprises a pressure sensor for sensing pressure within said gastrointestinal tract of said subject.

* * * * *